United States Patent
Rosenblatt et al.

(10) Patent No.: US 7,101,566 B2
(45) Date of Patent: *Sep. 5, 2006

(54) POLYMER COATED MICROPARTICLES FOR SUSTAINED RELEASE

(75) Inventors: Joel Rosenblatt, Watchung, NJ (US); Han Cui, Bridgewater, NJ (US); Ram L. Kataria, Hamilton Square, NJ (US); Chuanbin Wu, Franklin Park, NJ (US)

(73) Assignee: Ethicon, Inc., Somerville, NJ (US)

( * ) Notice: Subject to any disclaimer, the term of this patent is extended or adjusted under 35 U.S.C. 154(b) by 194 days.

This patent is subject to a terminal disclaimer.

(21) Appl. No.: 10/183,260

(22) Filed: Jun. 28, 2002

(65) Prior Publication Data

US 2004/0001890 A1 Jan. 1, 2004

(51) Int. Cl.
- A61F 13/00 (2006.01)
- A61F 2/00 (2006.01)
- A61K 9/14 (2006.01)
- A61K 9/19 (2006.01)

(52) U.S. Cl. .................. 424/423; 424/489; 424/490; 424/491; 424/493; 424/496; 424/497; 424/422

(58) Field of Classification Search ............... 424/450, 424/489, 490, 491, 493, 496, 497, 422, 423
See application file for complete search history.

(56) References Cited

U.S. PATENT DOCUMENTS

| | | | |
|---|---|---|---|
| 2,895,930 A | 7/1959 | Milton | |
| 3,806,479 A | 4/1974 | Cunningham et al. | |
| 3,978,203 A | 8/1976 | Wise | |
| 3,997,512 A | 12/1976 | Casey et al. | |
| 4,048,256 A | 9/1977 | Casey et al. | |
| 4,076,798 A | 2/1978 | Casey et al. | |
| 4,095,600 A | 6/1978 | Casey et al. | |
| 4,118,470 A | 10/1978 | Casey et al. | |
| 4,122,129 A | 10/1978 | Casey et al. | |
| 4,384,975 A | 5/1983 | Fong | |
| 4,419,139 A | 12/1983 | Gooch | |
| 4,568,559 A | 2/1986 | Nuwayser et al. | |
| 4,623,588 A * | 11/1986 | Nuwayser et al. | 428/402.24 |
| 5,137,743 A | 8/1992 | Zaks | |
| 5,155,246 A * | 10/1992 | Naskar et al. | 554/213 |
| 5,219,980 A | 6/1993 | Swidler | |
| 5,306,311 A | 4/1994 | Stone et al. | |
| 5,308,623 A * | 5/1994 | Fues et al. | 424/426 |
| 5,360,626 A * | 11/1994 | Iyengar et al. | 426/601 |
| 5,411,554 A | 5/1995 | Sopelianos et al. | |

(Continued)

FOREIGN PATENT DOCUMENTS

EP 422209 B1 3/1995

(Continued)

OTHER PUBLICATIONS

Brian Parkyn, F. Lamb and B. V. Clifton, "Polyesters vol. 2 Unsaturated Polyesters and Polyester Plasticisers." London Iliffe Books Ltd., New York American Elsevier Publishing Company, Inc., 1967 pp. 107-122.

(Continued)

*Primary Examiner*—S. Tran

(57) ABSTRACT

The present invention is directed to sustained release microparticle formulation for parenteral administration of biologically active substances, especially drugs. More specifically it relates to coated drug containing microparticles, wherein the coating is a synthetic, bioabsorbable, biocompatible polymeric wax that is the reaction product of a polybasic acid or derivative thereof, a polyol and a fatty acid, the polymeric wax having a melting point less than about 70° C., as determined by differential scanning calorimetry.

24 Claims, 2 Drawing Sheets

U.S. PATENT DOCUMENTS

| | | | |
|---|---|---|---|
| 5,442,033 | A | 8/1995 | Bezwada et al. |
| 5,464,929 | A * | 11/1995 | Bezwada et al. ............ 528/361 |
| 5,599,852 | A | 2/1997 | Sopelianos et al. |
| 5,607,687 | A | 3/1997 | Bezwada et al. |
| 5,618,552 | A | 4/1997 | Bezwada et al. |
| 5,628,993 | A | 5/1997 | Yamagata et al. |
| 5,631,015 | A | 5/1997 | Bezwada et al. |
| 5,653,992 | A | 8/1997 | Bezwada et al. |
| 5,670,478 | A * | 9/1997 | Stuchlik et al. ................ 514/11 |
| 5,698,213 | A | 12/1997 | Jamiolkowski et al. |
| 5,700,583 | A | 12/1997 | Jamiolkowski et al. |
| 5,725,881 | A | 3/1998 | Buchholz et al. |
| 5,728,752 | A | 3/1998 | Scopelianos et al. |
| 5,750,100 | A | 5/1998 | Yamagata et al. |
| 5,753,234 | A | 5/1998 | Lee et al. |
| 5,824,333 | A | 10/1998 | Scopelianos et al. |
| 5,859,150 | A | 1/1999 | Jamiolkowski et al. |
| 5,998,552 | A | 12/1999 | Gruber et al. |
| 6,074,660 | A | 6/2000 | Jamiolkowski et al. |
| 6,100,346 | A | 8/2000 | Jamiolkowski et al. |
| 6,110,501 | A * | 8/2000 | Redding et al. ............ 424/490 |
| 6,114,458 | A | 9/2000 | Hawker et al. |
| 6,120,787 | A | 9/2000 | Gustafsson et al. |
| 6,121,398 | A | 9/2000 | Wool et al. |
| 6,147,168 | A | 11/2000 | Jamiolkowski et al. |
| 6,224,894 | B1 | 5/2001 | Jamiolkowski et al. |
| 6,251,435 | B1 | 6/2001 | Jamiolkowski et al. |
| 6,268,329 | B1 | 7/2001 | Markussen |
| 6,335,383 | B1 | 1/2002 | Scopelianos et al. |
| 7,005,136 | B1 * | 2/2006 | Nathan et al. ............... 424/423 |
| 7,030,127 | B1 * | 4/2006 | Nathan et al. ............... 514/259 |
| 2001/0007771 | A1 | 7/2001 | Sullivan et al. |
| 2001/0012522 | A1 * | 8/2001 | Ottoboni et al. ............ 424/501 |
| 2001/0021377 | A1 | 9/2001 | Jamiolkowski et al. |
| 2002/0037301 | A1 | 3/2002 | De La Poterie |
| 2003/0147926 | A1 * | 8/2003 | Ebert et al. ................. 424/400 |
| 2003/0185752 | A1 | 10/2003 | Nathan et al. |
| 2003/0236310 | A1 * | 12/2003 | Nathan et al. ............ 514/772.4 |
| 2004/0161458 | A1 * | 8/2004 | Meinzer et al. ............. 424/456 |

FOREIGN PATENT DOCUMENTS

| | | | |
|---|---|---|---|
| EP | | 841361 A1 | 5/1995 |
| EP | | 747072 A | 12/1996 |
| EP | | 1 270 024 A | 1/2003 |
| WO | WO 88/03785 | A1 | 6/1988 |
| WO | WO 89/08694 | A1 | 9/1989 |
| WO | WO 90/12604 | A1 | 11/1990 |
| WO | WO 92/12645 | A1 | 8/1992 |
| WO | WO 93/08850 | A1 | 5/1993 |
| WO | WO 94/25079 | A1 | 11/1994 |
| WO | WO 95/33821 | A1 | 12/1994 |
| WO | WO 95/22318 | A1 | 8/1995 |
| WO | WO 94/15079 | A1 | 11/1995 |
| WO | WO 97/09367 | | 3/1997 |
| WO | WO 97/23606 | A1 | 7/1997 |
| WO | WO 99/29303 | A1 | 6/1999 |
| WO | WO 00/02950 | A1 | 1/2000 |
| WO | WO 00/35511 | A | 6/2000 |
| WO | WO 00/44808 | A1 | 8/2000 |
| WO | WO 01/07486 | A1 | 2/2001 |
| WO | WO 01/76649 | A | 10/2001 |

OTHER PUBLICATIONS

Temple C. Patton, "Alkyd Resin Technology—Formulating Techniques and Allied Calculations," Interscience Publishers, of John Wiley and Sons, New York—London 1962, pp. 13-31.

U.S. Appl. No. 10/112,554, A. Nathan et al.

U.S. Appl. No. 10/162,933, A. Nathan.

U.S. Appl. No. 10/178,970, A. Nathan.

U.S. Appl. No. 10/322,132, A. Nathan.

U.S. Appl. No. 10/322,177, S. C. Arnold.

U.S. Appl. No. 10/325,768, A. Nathan.

U.S. Appl. No. 10/323,387, A. Nathan.

U.S. Appl. No. 10/322,154, A. Nathan.

U.S. Appl. No 10/322,117, A. Nathan.

U.S. Appl. No. 10/112,201, A. Nathan et al.

Database WPI Week 199430 Derwent Publications Ltd., London, GB; an 1994-248859 XP002256761 & WO 94 15591 A. (Hisamitsu), Jul. 12, 1994 abstract.

Emiko Koyama, Fumio Sanda, and Takeshi Endo, "Synthesis of Poly(ester-amide)s Derived from Optically Active Amino Alcohols," Macromol. Symp., 122, 275-280 (1997).

Emiko Koyama, Fumio Sanda, and Takeshi Endo, "Polycondensations of Hydroxycarboxylic Acids Derived from Optically Active Aminoalcohols and Acid Anhydrides—Syntheses of Functional Poly(ester-amide)s," Journal of Polymer Science: Part A: Polymer Chemistry 35, 345-352 (1997).

Donald L. Elbert, Alison B. Pratt, Matthias P. Lutolf, Sven Halstenberg, Jeffrey A. Hubbell, "Protein Delivery from Materials Formed by Self-selective Conjugate Addition Reactions," Journal of Controlled Release, 76, 11-25 (2001).

* cited by examiner

POLYMER COATED MICROPARTICLES FOR SUSTAINED RELEASE

FIELD OF THE INVENTION

The present invention relates to sustained release microparticles for parenteral administration of therapeutic agents.

BACKGROUND OF THE INVENTION

Many drugs, proteins and peptides for use in medical therapy are susceptible to degradation at the site of administration. In addition, many of these therapeutic agents have very short in vivo half-lives. Consequently, multiple injections or multiple oral doses are required to achieve desirable therapy. It is desirable to increase the therapeutic efficacy of these therapeutic agents containing active ingredients by using parenterally administrable sustained release formulations with controlled release of the therapeutic agents.

A formulation intended for parenteral use has to meet a number of requirements in order to be approved by the regulatory authorities for use in humans. It has to be biocompatible and biodegradable and all substances used and their degradation products should be non-toxic. In addition, particulate therapeutic agents intended for injection have to be small enough to pass through the injection needle, which preferably means that they should be smaller than 200 microns. The agent should not be degraded to any large extent in the formulation during production or storage thereof or after administration and should be released in a biologically active form with reproducible kinetics.

Various dosage forms have been proposed for therapeutic agents that require parenteral administration. For example, an agent may be microencapsulation by a phase separation process using a coacervation agent such as mineral oil, vegetable oils or the like, resulting in the formation of a microparticle containing the agent.

Another microencapsulation method entails formation of a three-phase emulsion containing a therapeutic agent, a polymer, and water. A drying step yields microparticles of the agent microencapsulated in the polymer.

Also reported is the formation of microparticles by spray drying, rotary disc, or fluidized bed techniques combining biodegradable polymers and therapeutic agents.

As mentioned above, there is a need to control the release of the microencapsulated therapeutic agent from a parenterally administrable sustained release formulation of microparticles in an accurate way. Often, the initial release rate of agent is large. This is known as the initial burst of the agent from the microparticle. In many of the controlled release systems based on biodegradable polymers, the release rate and initial burst of the therapeutic agent is largely dependent on the amount of agent incorporated into the microparticle. This is due to the formation of channels in the microparticles at higher agent loadings.

A well-known way of controlling the release of therapeutic agent from solid core is to apply a synthetic, biodegradable polymer coating that produces a rate controlling film on the surface of the core particles. The release rate and initial burst of the therapeutic agent is controlled by factors including the thickness of the coating, the diffusivity of agent through the synthetic polymer comprising the coating, and the rate of biodegradation of the polymer.

Often, the method of applying the coating requires use of solvents to dissolve the coating polymer prior to the coating process. This is done in cases where the melting temperature of the polymer is high enough to cause changes in the performance of the agent.

Synthetic polymers may include aliphatic polyesters, polyanhydrides and poly(orthoester)s. Synthetic absorbable polymers typically degrade by a hydrolytic mechanism. Such synthetic absorbable polymers include homopolymers, such as poly(glycolide), poly(lactide), poly(e-caprolactone), poly(trimethylene carbonate) and poly(p-dioxanone), and copolymers, such as poly(lactide-co-glycolide), poly(e-caprolactone-co-glycolide), and poly(glycolide-co-trimethylene carbonate). The polymers may be statistically random copolymers, segmented copolymers, block copolymers or graft copolymers.

Alkyd-type polyesters prepared by the polycondensation of a polyol, polyacid and fatty acid are used in the coating industry in a variety of products, including chemical resins, enamels, varnishes and paints. These polyesters also are used in the food industry to make texturized oils and emulsions for use as fat substitutes.

There is a great need for polymers for use as coatings in parenteral therapeutic agent delivery, where the polymers have both low melting temperatures and low viscosities upon melting, thus permitting for solvent-free processing techniques in preparation of parenteral therapeutic agent delivery compositions, can crystallize rapidly, and biodegrade within 6 months.

SUMMARY OF THE INVENTION

The present invention is directed to sustained release microparticles for parenteral administration of therapeutic agents, especially drugs. More specifically it relates to microparticles having a core of a biodegradable polymer containing a therapeutic agent, and a coating, wherein the coating comprises a synthetic, bioabsorbable, biocompatible polymeric wax comprising the reaction product of a polybasic acid or derivative thereof, a fatty acid and a polyol, the polymeric wax having a melting point less than about 70° C., as determined by differential scanning calorimetry.

DETAILED DESCRIPTION OF THE INVENTION

The present invention provides a microparticle formulation comprising microparticles of a biodegradable polymer which contain a therapeutic agent and are coated with a film of a biodegradable polymer to provide accurate control of the release rate of the agent from microparticles.

Figure 1:
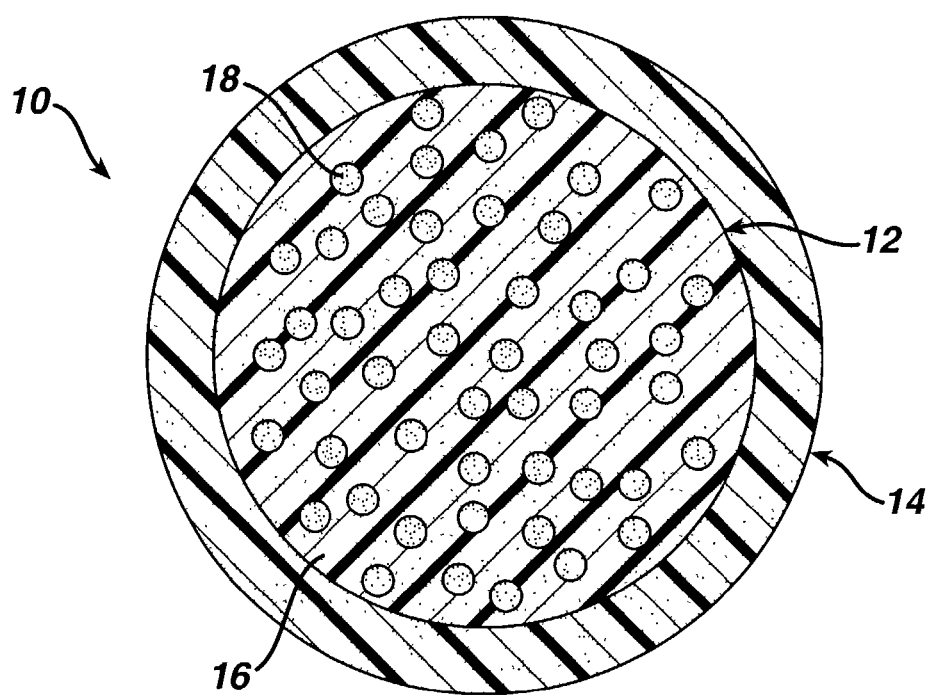
FIG. 1 is schematic drawing of the construct of coated microparticles of this invention.

A schematic drawing of the construct of coated microparticles of this invention are shown on FIG. 1. The figure shows microparticle 10 which has core 12 and coating layer 14. Core 12 has therapeutic agent 18 and pharmaceutical carrier 16. The diameter of microparticle 10 is less than about 200 microns, small enough to pass through the injection needle. In FIG. 1, therapeutic agent 18 is shown as spherical particles suspended in pharmaceutical carrier 16. One skilled in the art could envision therapeutic agent 18 as being non-spherical in shape. Also, therapeutic agent 18 may be soluble in pharmaceutical carrier 16, and core 12 would appear homogeneous in FIG. 1.

Synthetic polymers may be used as pharmaceutical carrier 16 in core 12 of microparticles 10. These polymers may include aliphatic polyesters, polyanhydrides and poly (orthoester)s. Synthetic absorbable polymers typically degrade by a hydrolytic mechanism. Such synthetic absorbable polymers include homopolymers, such as poly(glycolide), poly(lactide), poly(e-caprolactone), poly(trimethylene carbonate) and poly(p-dioxanone), and copolymers, such as poly(lactide-co-glycolide), poly(e-caprolactone-co-glycolide), and poly(glycolide-co-trimethylene carbonate). The polymers may be statistically random copolymers, segmented copolymers, block copolymers or graft copolymers.

Preferably, the synthetic, bioabsorbable, biocompatible polymers used as the pharmaceutical carrier 16 in core 12 of microparticles 10 alkyd polymers. Alkyd polymers have been prepared by several known methods. For example, alkyd-type polymers were prepared by Van Bemmelen (*J. Prakt. Chem.*, 69 (1856) 84) by condensing succinic anhydride with glycerol. In the "Fatty Acid" method (see Parkyn, et al. *Polyesters* (1967), Iliffe Books, London, Vol. 2 and Patton, In: *Alkyd Resins Technology*, Wiley-Interscience New York (1962)), a fatty acid, a polyol and an anhydride are mixed together and allowed to react. The "Fatty Acid-Monoglyceride" method includes a first step of esterifying the fatty acid with glycerol and, when the first reaction is complete, adding an acid anhydride. The reaction mixture then is heated and the polymerization reaction takes place. In the "Oil-Monoglyceride" method, an oil is reacted with glycerol to form a mixture of mono-, di-, and triglycerides. This mixture then is polymerized by reacting with an acid anhydride.

The coating layer 14 of microparticle 10 is an alkyd polymer in the form of a polymeric wax. The polymeric waxes utilized in the present invention are the reaction product of a polybasic acid or derivative thereof, a fatty acid, and a polyol, and may be classified as alkyd polyester waxes. As used herein, a wax is a solid, low-melting substance that is plastic when warm and, due to its relatively low molecular weight, is fluid when melted. Preferably, the polymeric waxes of the present invention are prepared by the polycondensation of a polybasic acid or derivative thereof and a monoglyceride, wherein the monoglyceride comprises reactive hydroxy groups and fatty acid groups. The expected hydrolysis byproducts are glycerol, dicarboxylic acid(s), and fatty acid(s), all of which are biocompatible. Preferably, the polymeric waxes utilized in the present invention will have a number average molecular weight between about 1,000 g/mole and about 100,000 g/mole, as determined by gel permeation chromatography. The polymeric waxes comprise an aliphatic polyester backbone with pendant fatty acid ester groups that crystallize rapidly, depending on the fatty acid chain length, and exhibit relatively low melting points, e.g. less than about 100° C., preferably less than about 70° C. More preferably, the melting point of the polymeric wax will be between about 25° C. and about 70° C. Typically, the polymeric waxes used in the present invention will be a solid at room temperature.

Fatty acids used to prepare polymeric waxes utilized in the present invention may be saturated or unsaturated and may vary in length from $C_{14}$ to $C_{30}$. Examples of such fatty acids include, without limitation, stearic acid, palmitic acid, myrisitic acid, caproic acid, decanoic acid, lauric acid, linoleic acid and oleic acid.

Polyols that can be used to prepare the polymeric waxes include, without limitation, glycols, polyglycerols, polyglycerol esters, glycerol, sugars and sugar alcohols. Glycerol is a preferred polyhydric alcohol due to its abundance and cost.

Monoglycerides which may be used to prepare polymeric waxes utilized in the present invention include, without limitation, monostearoyl glycerol, monopalmitoyl glycerol, monomyrisitoyl glycerol, monocaproyl glycerol, monodecanoyl glycerol, monolauroyl glycerol, monolinoleoyl glycerol, monooleoyl glycerol, and combinations thereof. Preferred monoglycerides include monostearoyl glycerol, monopalmitoyl glycerol and monomyrisitoyl glycerol.

Polybasic acids that can be used include natural multifunctional carboxylic acids, such as succinic, glutaric, adipic, pimelic, suberic, and sebacic acids; hydroxy acids, such as diglycolic, malic, tartaric and citric acids; and unsaturated acids, such as fumaric and maleic acids. Polybasic acid derivatives include anhydrides, such as succinic anhydride, diglycolic anhydride, glutaric anhydride and maleic anhydride, mixed anhydrides, esters, activated esters and acid halides. The multifunctional carboxylic acids listed above are preferred.

In certain embodiments of the invention, the polymeric wax may be prepared from the polybasic acid or derivative thereof, the monoglyceride and, additionally, at least on additional polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, other diols, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s.

In preparing the polymeric waxes utilized in the present invention, the particular chemical and mechanical properties required of the polymeric wax must be considered. For example, changing the chemical composition can vary the physical and mechanical properties, including absorption times. Copolymers can be prepared by using mixtures of diols, triol, polyols, diacids, triacids, and different monoalkanoyl glycerides to match a desired set of properties. Similarly, blends of two or more alkyd polyesters may be prepared to tailor properties for different applications.

Alkyd polyester waxes of the present invention can be made more hydrophobic by increasing the length of the fatty acid side chain or the length of the diacid in the backbone, or by incorporating a long chain diol. Alternatively, alkyd polyester waxes of the present invention can be made more hydrophilic or amphiphilic by employing hydroxy acids, such as malic, tartaric and citric acids, or some oxadiacids, in the composition, or by employing poly(ethylene glycol)s or copolymers of polyethylene glycol and polypropylene glycol, commonly known as Pluronics, in the formation of segmented block copolymers.

Copolymers containing other linkages in addition to an ester linkage also may be synthesized; for example, ester-amides, ester-carbonates, ester-anhydrides and ester urethanes, to name a few.

Multifunctional monomers may be used to produce crosslinked polymeric wax networks. Alternatively, double bonds may be introduced by using polyols, polyacids or fatty acids containing at least one double bond to allow photocrosslinking. Hydrogels may be prepared using this approach provided the polymer is sufficiently water soluble or swellable.

Functionalized polymeric waxes can be prepared by appropriate choice of monomers. Polymers having pendant hydroxyls can be synthesized using a hydroxy acid such as malic or tartaric acid in the synthesis. Polymers with pendent amines, carboxyls or other functional groups also may be synthesized.

The polymerization of the alkyd polyester preferably is performed under melt polycondensation conditions in the presence of an organometallic catalyst at elevated temperatures. The organometallic catalyst preferably is a tin-based catalyst e.g. stannous octoate. The catalyst preferably will be present in the mixture at a mole ratio of polyol and polycarboxylic acid to catalyst in the range of from about 15,000/1 to 80,000/1. The reaction preferably is performed at a temperature no less than about 120° C. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and melting temperature of the polymer. The preferred reaction conditions of temperature, time and pressure can be readily determined by assessing these and other factors.

Generally, the reaction mixture will be maintained at about 180° C. The polymerization reaction can be allowed to proceed at this temperature until the desired molecular weight and percent conversion is achieved for the copolymer, which typically will take from about 15 minutes to 24 hours. Increasing the reaction temperature generally decreases the reaction time needed to achieve a particular molecular weight.

In another embodiment, copolymers of alkyd polyesters can be prepared by forming an alkyd polyester prepolymer polymerized under melt polycondensation conditions, then adding at least one lactone monomer or lactone prepolymer. The mixture then would be subjected to the desired conditions of temperature and time to copolymerize the prepolymer with the lactone monomers. The molecular weight of the prepolymer, as well as its composition, can be varied depending on the desired characteristic that the prepolymer is to impart to the copolymer. Those skilled in the art will recognize that the alkyd polyester prepolymers described herein can also be made from mixtures of more than one diol or dioxycarboxylic acid.

The polymers, copolymers and blends of the present invention can be cross-linked to affect mechanical properties. Cross-linking can be accomplished by the addition of cross-linking enhancers, irradiation, e.g. gamma-irradiation, or a combination of both. In particular, cross-linking can be used to control the amount of swelling that the materials of this invention experience in water.

One of the beneficial properties of the alkyd polyester of this invention is that the ester linkages are hydrolytically unstable, and therefore the polymer is bioabsorbable because it readily breaks down into small segments when exposed to moist body tissue. In this regard, while it is envisioned that co-reactants could be incorporated into the reaction mixture of the polybasic acid and the diol for the formation of the alkyd polyester, it is preferable that the reaction mixture does not contain a concentration of any co-reactant which would render the subsequently prepared polymer nonabsorbable. Preferably, the reaction mixture is substantially free of any such co-reactants if the resulting polymer is rendered nonabsorbable.

To form core 12 of microparticle 10, the polymer used as pharmaceutical carrier 16 in core 12 would be mixed with an effective amount of therapeutic agent 18. Common microencapsulation methods include rotating disk, spray drying, fluidized bed, or three-phase emulsion techniques.

The preferred technique for preparing drug-containing microparticles of the present invention is the use of a rotating disk technique. The polymer used as pharmaceutical carrier 16 in core 12 would be blended with therapeutic agent 18 at a temperature above the melting point of the polymer. The blend is then fed at a controlled rate to the center of a rotary disk that is heated to ensure that the blend remained in a liquid state on the surface of the disk. The rotation of the disk causes a thin liquid film of drug/polymer blend to be formed on the surface the disk. The liquid film is thrown radially outward from the surface of the disk and droplets solidify as before they are collected. The processing is done under a nitrogen blanket to prevent polymer degradation at the elevated temperatures. The microparticles made using this process had a mean particle size of about 50–150 m.

The polymeric waxes described above are used in coating layer 14 of microparticle 10. The polymeric wax may be applied as a coating using conventional fluidized bed coating processes. In the fluidized bed coating process, microparticles formed as described above are first suspended in an upwardly-moving gas stream in a coating chamber. The polymeric wax coating material, dissolved in a solvent, or, preferably as a melt, is sprayed into the moving fluid bed of microparticles to coat the microparticles. The coated microparticles are recovered, and any residual solvent is removed.

Most preferably, the polymeric waxes of the current invention are used as both the pharmaceutical carrier 16 and the coating layer 14 of microparticle 10. In this embodiment, the bond between coating layer 14 and core 16 should be excellent. The amount of polymeric wax to be applied on the surface of microparticle 10 can be readily determined empirically, and will depend on the specific application where a sustained release or a moderately sustained release is need.

Suitable diluents and carriers are those which are generally useful in pharmaceutical formulations for aid in injection purposes. Diluents include, but are not limited to, physiological saline solution; vegetable oil; a glycol base solvent such as polyethylene glycol, propylene glycol, glycerol formal or the mixture of them; mono, di and triglycerides and the like. Viscosity enhancing agents as diluents include, but are not limited to, aqueous solution of any one from the following or a mixture selected from at lease two of: alginic acid, bentonite, carbomer, carboxymethylcellulose calcium, carborymethylcellulose sodium, carragenan, cellulose, carboxymethylcellulose disodium, dextrin, gelatine, guar gum, hydroxyethyl cellulose, hydroxyproyl cellulose, hydroxypropyl methylcellulose, magnesium aluminium silicate, methylcellulose, pectin, polyethylene oxide, silicon dioxide, colloidal silicon dioxide, sodium alginate, Tragacanth, xanthan gum. The aqueous solution of those viscosity-enhancing agents as diluents may also contain a surfactant.

Suitable excipients and stabilizers are those which are generally useful in pharmaceutical formulations. Among the ingredients useful for such preparations the following are of special interest: acidifying agents (citric acid, fumaric acid, hydrochloric acid, malic acid, phosphoric acid, propionic acid, sulfuric acid, and tartaric acid), alkalizing agents (ammonia solution, ammonium carbonate, potassium hydroxide, sodium bicarbonate, sodium borate, sodium carbonate, sodium hydroxide, di-sodium tartrate, and succinic acid-disodium hexahydrate), and antioxidants (1-ascorbic acid, ascorbyl palmitate, calcium ascorbate, and dilauryl thiodipropionate).

The variety of therapeutic agents 18 that can be used in the coated microparticles 10 of the invention is vast. In general, therapeutic agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics.

The microparticles may be administered in any suitable dosage form such as oral, parenteral, subcutaneously as an implant, vaginally or as a suppository. The therapeutic agent may be present as a liquid, a finely divided solid, or any other appropriate physical form. Typically, but optionally, the microparticles will include one or more additives, such as, but not limited to, nontoxic auxiliary substances such as diluents, carriers, excipients, stabilizers or the like. Other suitable additives may be formulated with the polymeric wax and therapeutic agent or compound.

The amount of therapeutic agent will be dependent upon the particular drug employed and medical condition being treated. Typically, the amount of agent represents about 0.001% to about 70%, more typically about 0.001% to about 50%, most typically about 0.001% to about 20% by weight of the core of the microparticle.

The quantity and type of alkyd polyester wax incorporated into the parenteral will vary depending on the release profile desired and the amount of agent employed. The product may contain blends of polyesters to provide the desired release profile or consistency to a given formulation.

The alkyd polyester wax, upon contact with body fluids including blood or the like, undergoes gradual degradation, mainly through hydrolysis, with concomitant release of the dispersed therapeutic agentfor a sustained or extended period, as compared to the release from an isotonic saline solution. This can result in prolonged delivery, e.g. over about 1 to about 2,000 hours, preferably about 2 to about 800 hours) of effective amounts, e.g. 0.0001 mg/kg/hour to 10 mg/kg/hour) of the agent. This dosage form can be administered as is necessary depending on the subject being treated, the severity of the affliction, the judgment of the prescribing physician, and the like.

Individual formulations of therapeutic agents and alkyd polyester wax may be tested in appropriate in vitro and in vivo models to achieve the desired agent release profiles. For example, an agent could be formulated with an alkyd polyester wax and orally administered to an animal. The release profile could then be monitored by appropriate means, such as by taking blood samples at specific times and assaying the samples for agent concentration. Following this or similar procedures, those skilled in the art will be able to formulate a variety of formulations.

The examples set forth below are for illustration purposes only, and are not intended to limit the scope of the claimed invention in any way. Numerous additional embodiments within the scope and spirit of the invention will become readily apparent to those skilled in the art.

In the examples below, the synthesized polymeric waxes were characterized via differential scanning calorimetry (DSC), gel permeation chromatography (GPC), and nuclear magnetic resonance (NMR) spectroscopy. DSC measurements were performed on a 2920 Modulated Differential Scanning Calorimeter from TA Instruments using aluminum sample pans and sample weights of 5–10 mg. Samples were heated from room temperature to 100° C. at 10° C./minute; quenched to −40° C. at 30° C./minute followed by heating to 100° C. at 10° C./minute. For GPC, a Waters System with Millennium 32 Software and a 410 Refractive Index Detector were used. Molecular weights were determined relative to polystyrene standards using THF as the solvent. Proton NMR was obtained in deuterated chloroform on a 400 MHz NMR spectrometer using Varian software.

EXAMPLE 1

Synthesis of Poly(Monostearoyl Glycerol-co-succinate)

The copolymer was made in an 8CV Helicone Mixer Manufactured by Design Integrated Technology, Inc. of Warrenton, Va. 2510.5 grams (6.998 moles) of monostearoyl glycerol was weighed into a polyethylene bage. 700.4 grams (7.004 moles) of Succinic Anhydride was added to a 3 liter glass beaker. The 1.41 ml of a 0.33 Molar Stannous Octoate solution is drawn into a 2.00 ml glass syringe. All 3 materials are covered and transferred to the 8CV reactor. The stirrer turned on to 8 rpm reverse for 30 minutes then the reactor was left under full vacuum for at least 5 hours. The vacuum was 0.43 mmHg. Oil jacket temperature was set at 180° C. Stirring was set at 8 rpm reverse. Recorded the time of oil jacket inlet temperature had reached 180° C. as time zero for polymerization. Reaction lasted for 46.5 hours at 180° C. Polymer was discharged into clean aluminum pie pan. Once the solution crystallized, it was deglassed and cleaned of any glass fragments. The polymer was an amber colored solid.

DSC measurements found a melt temperature of 46.84° C., and a specific heat of 63.57 J/gm. GPC measurement determined a number average molecular weight of 2,932, and a weight average molecular weight of 38,422. The $^1$H NMR showed the following peaks: δ0.86 triplet (3H), 1.26 multiplet (28H), 1.61 multiplet (2H), 2.30 multiplet (2H), 2.65 multiplet (4H), 4.16 multiplet (2H), 4.34 multiplet (2H), and 5.28 multiplet (2H).

EXAMPLE 2

Sustained Release of Risperidone from Poly(Monostearoyl Glycerol-co-succinate) Microparticles in Vitro Poly(monostearoyl glycerol-co-succinate), or MGSA, polymer was prepared as described in Example 1. 10 grams of the polymer was placed in a 50-ml beaker and heated to 110° C. to melt the polymer. 3.34 grams of a drug in the form of a powder, Risperidone, sold by Janssen Pharmaceutica Inc., Beerse, Belgium, under the tradename RISPERDAL, was dispersed and suspended into the polymer melt using a magnetic stirrer to form a 25 percent by weight drug in polymer blend. A gradient heating mechanism was used to limit the exposure of the drug to the polymer melt at elevated temperature to few seconds.

The drug/polymer blend was converted to drug/polymer microparticles on a rotating disk apparatus. The drug/polymer blend first was equilibrated to 110° C. and then fed at a controlled rate of 3.5 grams/sec to the center of a 4-inch rotary disk that was run at 8000 rpm. The disk surface was heated using an induction heating mechanism to 130° C. to ensure that the drug/polymer blend was in a liquid state on the surface of the disk. The rotation of the disk caused a thin liquid film of drug/polymer blend to be formed on the surface the disk. The liquid film was thrown radially outward from the surface of the disk and droplets solidified upon contact with nitrogen in the rotating disk apparatus chamber to form drug/polymer microparticles. The processing was conducted under a nitrogen blanket to prevent polymer degradation at elevated temperatures. The solid microparticles were then collected using a cyclone separator. The Risperidone loaded MGSA microparticles made using this process had a mean particle size of about 100 microns.

Three 50-gram batches of blended particles were then prepared by blending 45 grams of sugar spheres (Paulaur Co., Cranbury, N.J.), with a size range of between 40 and 60 mesh, and 5 grams of Risperidone loaded MGSA microparticles prepared above. The sugar spheres and Risperidone loaded MGSA microparticles were blended in a Wurster Chamber (Niro MP-Micro precision coater, Aeromatic-Fielder Ltd., Eastleigh Hampshire, UK).

Coating solution was prepared by dissolving 25 grams of MGSA polymer prepared in Example 1 in 100 grams of chloroform.

Three samples of coated particles were then prepared. For the first sample, one batch of blended particles was loaded into a fluidized coater (Niro MP-Micro precision coater, Aeromatic-Fielder Ltd., Eastleigh Hampshire, UK). 1.8 grams of MGSA/chloroform solution was then added to the fluidized coater. The coating parameters were set as follows:

| | |
|---|---|
| Atomization pressure | 2.0 Bar |
| Atomization nozzle | 0.8 mm |
| Inlet temperature | 55.0 ° C. |
| Outlet temperature | 31–32 ° C. |
| Flow rate of coating solution | 0.5 grams/min |
| Fluidization air volume | 2.50–3.50 m$^3$/h |

Coated particles were collected from the fluidized coater and sieved to a size range of between 40 and 60 mesh. The MGSA coating on the coated particles was approximately 9 percent by weight.

Following the same coating procedure as outlined above, coated particles with approximately 20 and 30 percent by weight of MGSA coating were prepared. In these cases, however 4 and 6 grams, respectively, of MGSA/chloroform solution was then added to the fluidized coater.

All coated particles were stored in a vacuum oven until further testing was conducted.

In vitro release studies were performed with the coated particles in a buffer medium under physiological conditions. Approximately 20 mg of coated particles were placed in 50-ml test tubes. 30 ml of phosphate buffered saline solution were added to the test tubes. The test tubes were placed in a constant temperature water bath, and kept at 37° C. for the duration of the test. To determine drug release from the coated particles at each time point, 5 ml of buffer was removed and filtered through a 0.2 m filter. The amount of drug released was determined by HPLC measurements on an HP1100 instrument against risperidone standards.

Figure 2:
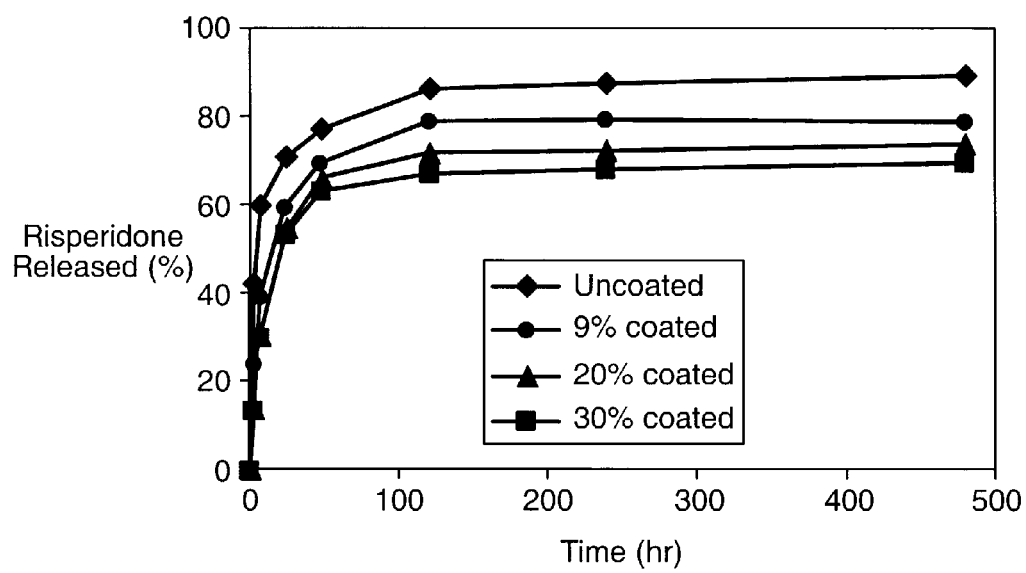
FIG. 2 is a plot of sustained release of Risperidone from coated and uncoated microparticles.

In vitro release versus time for the coated particles is shown in FIG. 2. The figure shows that risperidone release decreases with increasing coating level.

EXAMPLE 3

Sustained Release of Theophylline from Poly(Monostearoyl Glycerol-co-succinate) Microparticles in Vitro Poly(monostearoyl glycerol-co-succinate) polymer was prepared as described in Example 1. Appropriate amounts of polymer were melted as described in Example 2, and blended with amounts of a drug, Theophylline, as described in Example 2, to form 25% drug in polymer blends.

Figure 3:
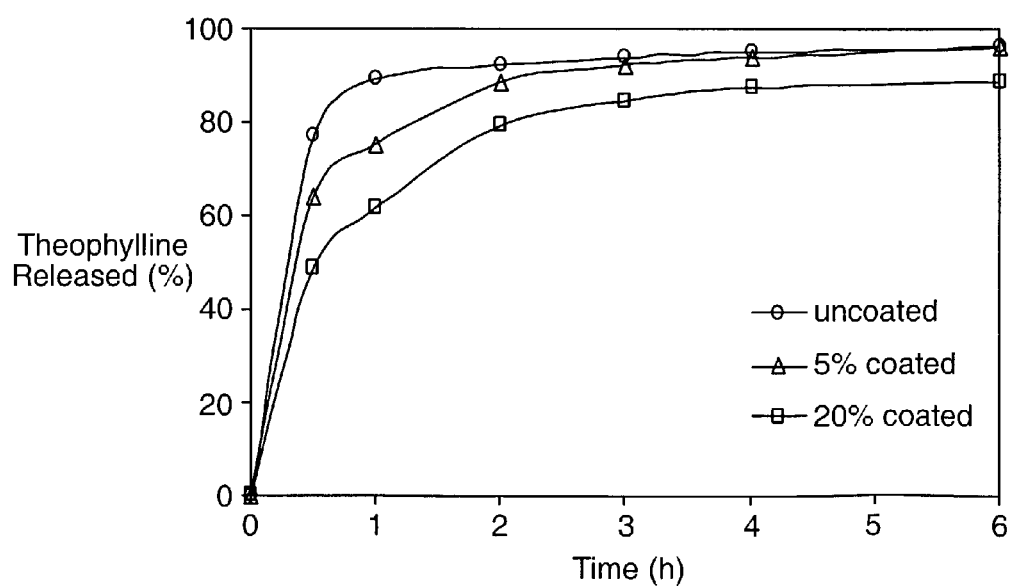
FIG. 3 is a plot of sustained release of Theophylline from coated and uncoated microparticles.

The drug/polymer blend was converted to drug/polymer microparticles on a rotating disk apparatus, and coated with different levels of poly(monostearoyl glycerol-co-succinate) polymer as described in Example 2. In vitro release studies were performed with these microparticles in a buffer medium at physiological conditions as described in Example 3, and release coated microparticles is shown in FIG. 3. The figure shows that increasing the polymer coating level on the microparticles decreases both the cumulative theophylline release from coated microspheres, as well as the burst release in the first hour of the study.

We claim:

1. Sustained release microparticles for parenteral administration of a therapeutic agent comprising: a core comprising a biodegradable polymer and therapeutically effective amount of said therapeutic agent, and a coating comprising a synthetic, bioabsorbable, biocompatible polymeric wax comprising the reaction product of a polybasic acid or derivative thereof and a monoglyceride, said monoglyceride is selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol, said polymeric wax comprising an aliphatic polyester backbone with pendant fatty acid ester groups and having a melting point less than about 70° C., as determined by differential scanning calorimetry.

2. The microparticles of claim 1 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid, fumaric acid, maleic acid, maleic anhydride, mixed anhydrides, esters, activated esters and acid halides.

3. The microparticles of claim 1 wherein said polybasic acid derivative is succinic anhydride.

4. The microparticles of claim 1 wherein said polybasic acid is succinic acid.

5. The microparticles of claim 1 wherein said polymeric wax has a number average molecular weight between about 1,000 g/mole and about 100,000 g/mole, as measured by gel permeation chromatography using polystyrene standards.

6. The microparticles of claim 1 wherein said polymeric wax is branched.

7. The microparticles of claim 1 wherein said polymeric wax comprises a copolymer.

8. The microparticles of claim 7 wherein said polymeric wax copolymer comprises the reaction product of said fatty acid, said polyol, and at least two of said polybasic acids or derivatives thereof selected from the group consisting of succinic acid, succinic anhydride, malic acid, tartaric acid, citric acid, diglycolic acid and diglycolic anhydride.

9. The microparticles of claim 7 wherein said polymeric wax copolymer comprises the reaction product of said polybasic acid or derivative thereof, and at least two monoglycerides selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

10. The microparticles of claim 7 wherein said wax copolymer comprises the reaction product of said polybasic acid or derivative thereof, a monoglyceride selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol, and at least one additional polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, other diols, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s.

11. The microparticles of claim 1 wherein said therapeutic agent is selected from the group consisting of antiinfectives, analgesics, anorexics, antihelmintics, antiarthritics, antiasthmatics, anticonvulsants, antidepressants, antidiuretics, antidiarrheals, antihistamines, antiinflammatory agents, antimigraine preparations, antinauseants, antineoplastics, antiparkinsonism drugs, antipruritics, antipsychotics, antipyretics, antispasmodics, anticholinergics, sympathomimetics, xanthine derivatives, calcium channel blockers, beta-blockers, antiarrhythmics, antihypertensives, diuretics, vasodilators, central nervous system stimulants,decongestants, hormones, steroids, hypnotics, immunosuppressives, muscle relaxants, parasympatholytics, psychostimulants, sedatives, tranquilizers, naturally derived or genetically engineered proteins, polysaccharides, glycoproteins, or lipoproteins, oligonucleotides, antibodies, antigens, cholinergics, chemotherapeutics, hemostatics, clot dissolving agents, radioactive agents and cystostatics.

12. The microparticles of claim 1 wherein said polymeric wax has a melting point between about 25° C. and about 70° C.

13. The microparticles of claim 1 wherein said biodegradable polymer of said core comprises a second synthetic, bioabsorbable, biocompatible polymeric wax comprising the reaction product of a polybasic acid or derivative thereof, a fatty acid; and a polyol, said polymeric wax having a melting point less than about 70° C., as determined by differential scanning calorimetry.

14. The microparticles of claim 13 wherein said second polymeric wax comprises the reaction product of said polybasic acid or derivative thereof and a monoglyceride, said monoglyceride comprising the reaction product of said fatty acid and said polyol.

15. The microparticles of claim 14 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid, fumaric acid, maleic acid, maleic anhydride, mixed anhydrides, esters, activated esters and acid halides.

16. The microparticles of claim 14 wherein said monoglyceride is selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

17. The microparticles of claim 16 wherein said polybasic acid derivative is succinic anhydride.

18. The microparticles of claim 16 wherein said polybasic acid is succinic acid.

19. The microparticles of claim 13 wherein said second polymeric wax has a number average molecular weight between about 1,000 g/mole and about 100,000 g/mole, as measured by gel permeation chromatography using polystyrene standards.

20. The microparticles of claim 13 wherein said second polymeric wax is branched.

21. The microparticles of claim 13 wherein said second polymeric wax comprises a copolymer.

22. The microparticles of claim 21 wherein said polymeric wax copolymer comprises the reaction product of said fatty acid, said polyol, and at least two of said polybasic acids or derivatives thereof selected from the group consisting of succinic acid, succinic anhydride, malic acid, tartaric acid, citric acid, diglycolic acid and diglycolic anhydride.

23. The microparticles of claim 21 wherein said polymeric wax copolymer comprises the reaction product of said polybasic acid or derivative thereof, and at least two monoglycerides selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

24. The microparticles of claim 21 wherein said wax copolymer comprises the reaction product of said polybasic acid or derivative thereof, a monoglyceride selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol, and at least one additional polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, other diols, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s.

* * * * *